United States Patent

Radis et al.

[11] Patent Number: 5,980,577
[45] Date of Patent: Nov. 9, 1999

[54] PROTECTIVE ITEM SUPPORTING AN APPENDAGE

[76] Inventors: Vasilis Radis, 15 Arilia St., Balcatta; Tanasis Radis, 105 Duke St., Scarborough, both of Wash.

[21] Appl. No.: 08/847,198

[22] Filed: May 1, 1997

[51] Int. Cl.⁶ ............................................. A61F 2/80
[52] U.S. Cl. ........................... 623/36; 623/33; 623/34; 623/35
[58] Field of Search .................... 623/33, 34, 35, 623/36, 37, 56

[56] References Cited

U.S. PATENT DOCUMENTS

| | | | |
|---|---|---|---|
| 2,634,424 | 4/1953 | O'Gorman | 623/37 |
| 2,671,225 | 3/1954 | Schoere et al. | 623/36 |
| 3,889,301 | 6/1975 | Bonner, Sr. . | |
| 4,595,172 | 6/1986 | Henderson . | |
| 4,655,779 | 4/1987 | Jarowiak | 623/37 |
| 5,108,456 | 4/1992 | Coonan, III | 623/37 |
| 5,133,776 | 7/1992 | Crowder . | |
| 5,139,523 | 8/1992 | Paton et al. | 623/37 |
| 5,156,629 | 10/1992 | Shane et al. . | |
| 5,314,496 | 5/1994 | Harris et al. | 623/36 X |
| 5,387,245 | 2/1995 | Fay et al. | 623/37 |
| 5,507,836 | 4/1996 | Pohlig | 623/36 X |
| 5,549,709 | 8/1996 | Caspers | 623/37 |
| 5,658,353 | 8/1997 | Layton | 623/33 |
| 5,702,489 | 12/1997 | Slemker | 623/36 |

FOREIGN PATENT DOCUMENTS

| | | |
|---|---|---|
| 35864/89 | 12/1969 | Australia . |
| 0 019 612 | 11/1980 | European Pat. Off. . |
| 0 363 654 | 4/1990 | European Pat. Off. . |
| 0 363 654 A2 | 4/1990 | European Pat. Off. . |
| 2420335 | 10/1979 | France ..................................... 623/37 |
| 175973 | 9/1993 | Germany ................................. 623/37 |
| 715534 | 6/1995 | Japan . |
| 1337080 | 9/1987 | Russian Federation . |
| WO 84/00881 | 3/1984 | WIPO . |
| WO 92/08425 | 5/1992 | WIPO . |
| WO 93/15695 | 8/1993 | WIPO ..................................... 623/37 |
| WO 94/27526 | 12/1994 | WIPO . |

OTHER PUBLICATIONS

Examiner's first report from the Australian Patent Office dated Jun. 24, 1997.

*Primary Examiner*—Paul B. Prebilic
*Attorney, Agent, or Firm*—Merchant & Gould P.C.

[57] ABSTRACT

An improvement to a protective item capable of supporting a load bearing appendage, said item comprising a space having an opening, said space being configured to snugly receive the appendage, said improvement comprising a fluid pathway communicating between the exterior of the item and the inner end of the space, said improvement further comprising a flow control valve located in said fluid pathway enabling a uni-directional flow of air from the exterior to the space.

17 Claims, 3 Drawing Sheets

PROTECTIVE ITEM SUPPORTING AN APPENDAGE

The present invention relates to a improvement to a prosthesis where the prosthesis is capable of supporting a persons load bearing appendage.

Throughout the specification the term "prosthesis" shall be taken as comprising a prosthesis capable of receiving a stump of a person's amputated limb.

DESCRIPTION OF THE PRIOR ART

A particular example of an item to which the invention relates comprises a leg prosthesis worn by amputees. A primary difficulty which has in the past been experienced with leg prostheses is the lack of ventilation into the space which accommodates the leg stump. As a result of this lack of ventilation and the perspiration which is generated from the portion of the appendage located within that space, difficulties can arise including skin ailments and in the generation of lesions on the stump which can in some cases be the source of severe infections. The occurrence of such ailments severely limits the utilisation of the prosthesis. Therefore while the purpose of leg prostheses is to facilitate the mobility of an amputee, it has been found that because of the difficulties created by the accommodation of the leg stump in the prosthesis and the extreme discomfort which can be experienced when the prosthesis is being worn, the amount of time that the prosthesis can be worn is very limited.

It has been found however that if air is permitted to circulate within the space accommodating the appendage, some of the above difficulties can be avoided and this can be particularly so if air can be forcibly directed through the space.

In addition, since the prosthesis must accommodate the leg stump in a very snug manner the inner end of the space accommodating the stump becomes sealingly separated from the exterior. As a result, the space between the inner portion of the leg stump and the wall of the socket within the prosthesis becomes isolated. The result of such is that when the prosthesis is in use, the space will vary in volume with each step of the person whereby during the downstep the space is reduced in volume and during the upstep the space will increase in volume. It has been found that the increase in volume of the space creates a negative pressure in the space between the stump and the prosthesis which causes the skin of the leg stump to be pulled into the space and into close contact with the liner within the space. This action upon the skin serves to increase the degree of contact between the skin and the liner resulting in considerable chaffing being experienced on the skin of the leg stump and discomfort to the wearer which only serves to compound the discomfort to the wearer.

In addition, it has been found that the shock loads which are exerted on the leg stump during use of the prosthesis can cause extreme discomfort particularly after atrophication of the muscle tissue in the region of the stump which causes the residual bone in the stump to be in close contact with the inner surface of the socket of the prosthesis.

SUMMARY OF THE INVENTION

It is an object of the invention to provide an improvement to a prosthesis which can at least partially eliminate some of the difficulties which are referred to above.

Accordingly, the invention resides in an improvement to a prosthesis where said prosthesis comprises a socket which is configured to snugly receive the stump, said improvement comprising a fluid pathway communicating between the exterior of the socket and an outlet at the inner end of the socket, said improvement further comprising a one-way valve located in the fluid pathway and positioned to provide a uni-directional flow of air into the inner end of the socket such that in use the fluid pressure between the stump and the socket at the inner end of the socket will be maintained at a pressure substantially not less than ambient pressure.

According to a preferred feature of the invention, the fluid pathway has an outlet into said space which comprises a plurality of openings.

According to an embodiment the improvement is applied to a leg prosthesis where the space accommodates the stump of the leg. According to a preferred feature of the embodiment, the leg prosthesis includes a liner which is receivable over the stump and which is receivable in the socket, where the liner is formed with one or more openings in the region of the outlet. According to another preferred feature of the embodiment the fluid pathway is provided within the body of the liner.

The invention will be more fully understood in the light of the following description of several specific embodiments. The description is made with reference to the accompanying drawings of which:

DETAILED DESCRIPTION OF A PREFERRED EMBODIMENT

Figure 1:
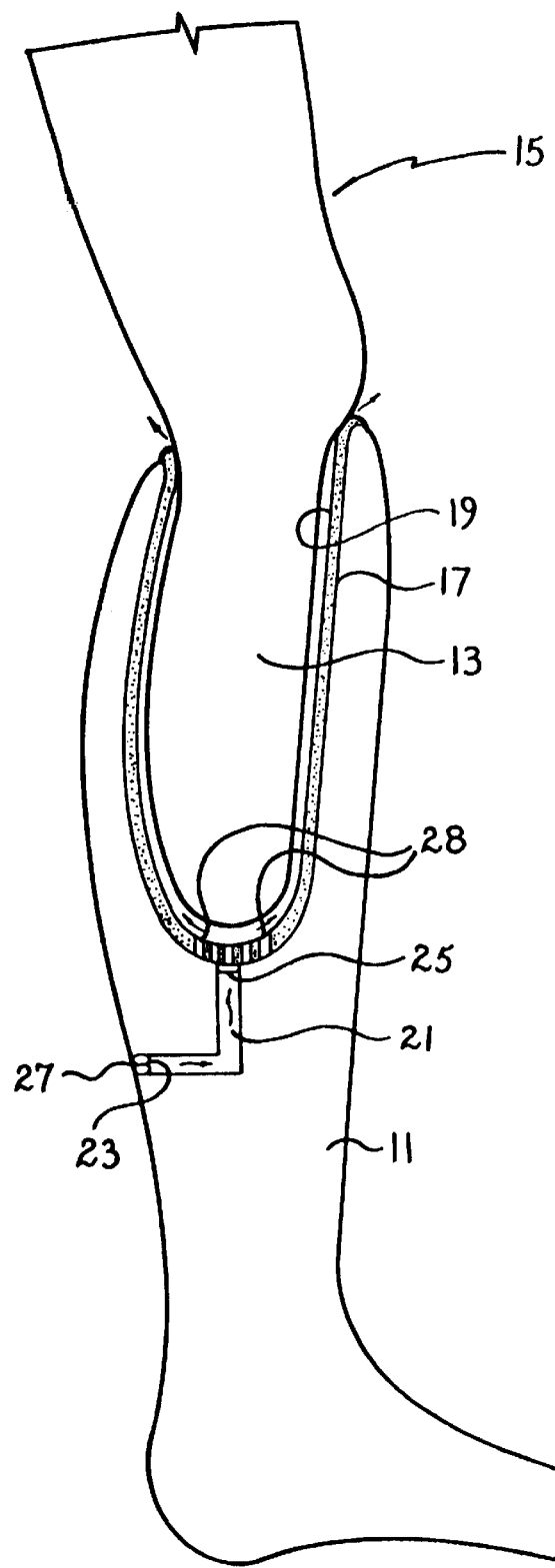
FIG. 1 is a schematic illustration of a leg stump accommodated within a leg prosthesis incorporating the first embodiment of the invention.

The first embodiment as shown at in the accompanying drawing relates to an improvement to a leg prosthesis 11 which accommodates the stump 13 of a leg 15. The leg prosthesis 11 generally comprises a socket 17 which has a configuration generally conforming to that of the stump 13. The prosthesis also generally includes a liner 19 which is intended to be received within the socket 17 and which is configured to be snugly received over the stump 13. It is also usual to cover the stump 125 with a sock (not shown) formed of a suitable fabric.

As stated previously there are several difficulties which have in the past been experienced with such prostheses which can create extreme discomfort for the wearer and thus reduce the utilisation of the prosthesis 11. One of these difficulties relates to the shock loadings which are exerted upon the stump 13 as a result of a normal walking action. It is usual that after some time the muscle tissue in the region of the stump 13 will suffer from atrophy which means that there is usually a very close spacing between the residual bone within the stump and the wall of the socket of the prosthesis. As a result, any shock loadings which are exerted upon the prosthesis as a result of a normal walking action are transmitted directly to the lower end of the bone. A further difficulty arises from the perspiration which is generated by the stump 13 within the socket. This perspiration creates a very moist warm environment which can cause degeneration of the skin of the stump resulting in lesions such as ulcers. A further difficulty that is experienced with conventional prostheses comprises the circumstance that the pressure within space between the liner 19 and the stump is caused to vary with the normal use of the stump. This can occur particularly where the liner is a very good fit on the stump, and is merely as a result of the relative movement between the leg 15 and the prosthesis 11 which results from a walking action. Although such movement may be small, it does result in the generation of a negative pressure within that space during the upstep which causes the skin of the stump to be pulled into that space and a higher pressure during the downstep. This cyclic action can generate a chaffing action on the stump which together with the moist warm environment created within that space can exacerbate the creation of lesions on the skin of the stump.

The first embodiment is intended to provide a means of at least reducing some of the severity of some of the difficulties referred to above. The improvement comprises a fluid pathway in the form of a passageway 21 extending between an inlet 23 provided on the outer surface of the prosthesis and an outlet 25 provided at the innermost end of the socket 17. The passageway 21 accommodates a control valve 27, at or in the vicinity of the inlet 23 which serves to control the air flow through the passageway to permit only a uni-directional flow of air from the inlet 23 to the outlet 25. In addition, the liner 19 is provided with one or more openings 28 in the region of the outlet 25 to enable air to flow from the outlet 25 to the space between the stump 13 and the liner.

In normal use of a prosthesis 11 incorporating the improvement of the first embodiment, the sequential and periodic variation of the volume of the space between the leg stump 13 and the liner 19 which results from a normal walking action serves to effect a repetitive delivery of air into the space between the liner and the stump 19 of the leg 15. During the upstep, the relative movement of the prosthesis 11 away from the lower end of the stump 13 causes the space between the stump 13 and liner 19 to increase in volume. Because of the close engagement of the upper end of the liner 19 with the leg that increase in volume results in a decrease in pressure which serves to draw air into the lower end of the space between the stump 13 and liner 19 through the passageway 21. During the downstep the movement of the stump 13 relative to the liner 19 causes the space therebetween to be reduced in volume however the valve 27 prevents any air to escape from space through the passageway. This creates an air cushion between the stump 13 and the liner 19 which serves to reduce the shock loading exerted upon the stump 13, since the pressurised cushion of air so created seems to initially support a substantial portion of the weight of the wearer during the down step and when standing. In addition, the air cushion serves to separate the skin of the stump 13 from the liner 19 to reduce the degree of contact and the consequent chaffing and creation of pressure spots and abrasion which in turn will significantly reduce the pain experienced by the wearer. The pressurisation of the air in the socket also causes at least some of the air within the space to be forced upwardly through the space to be forced out of the space between the junction of the upper end of the liner 19 with the stump 13. This flow of air serves to evaporate any moisture which is generated as a result of perspiration on the leg stump which can reduce the likelihood of infection. Furthermore, the introduction of air into the between the stump and liner space during the upstep serves to prevent the generation of a negative pressure in that space which eliminates the movement of the skin of the stump 13 into engagement with the liner 19 or the exertion of any forces upon the skin which has previously been a feature of prostheses as a result of the generation of the negative pressure in that space.

Figure 2:
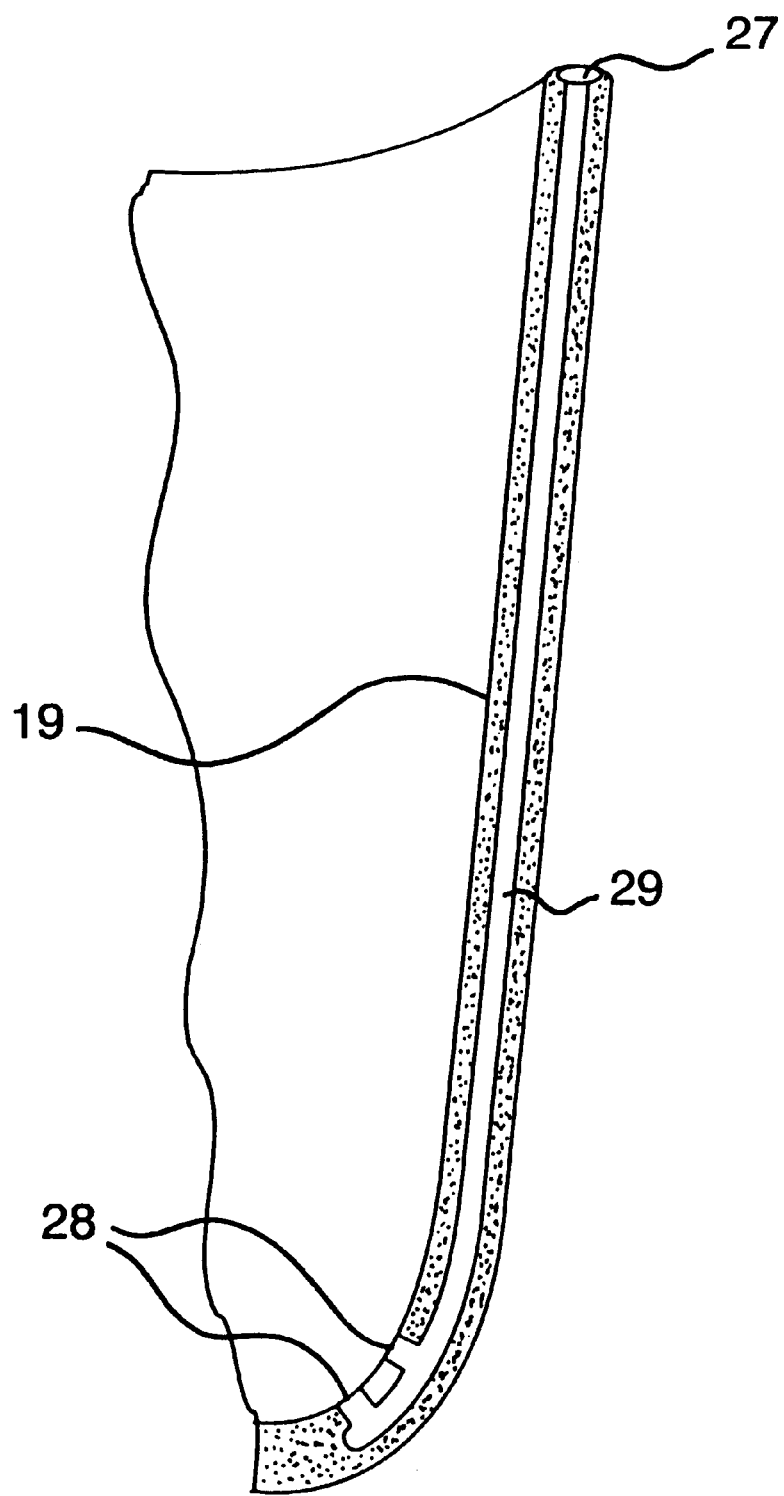
FIG. 2 is a schematic sectional view of a liner incorporating the second embodiment of the invention.

According to an alternative embodiment of the invention, the position of the passageway need not take the particular position shown in the drawings and can be located in any suitable location. In a second embodiment as shown at FIG. 2, the passageway 29 is accommodated within the body of the liner where the inlet and valve 27 are located in the upper edge of the liner and the outlet openings are located in the region of the inner space accommodating the stump.

Figure 3:
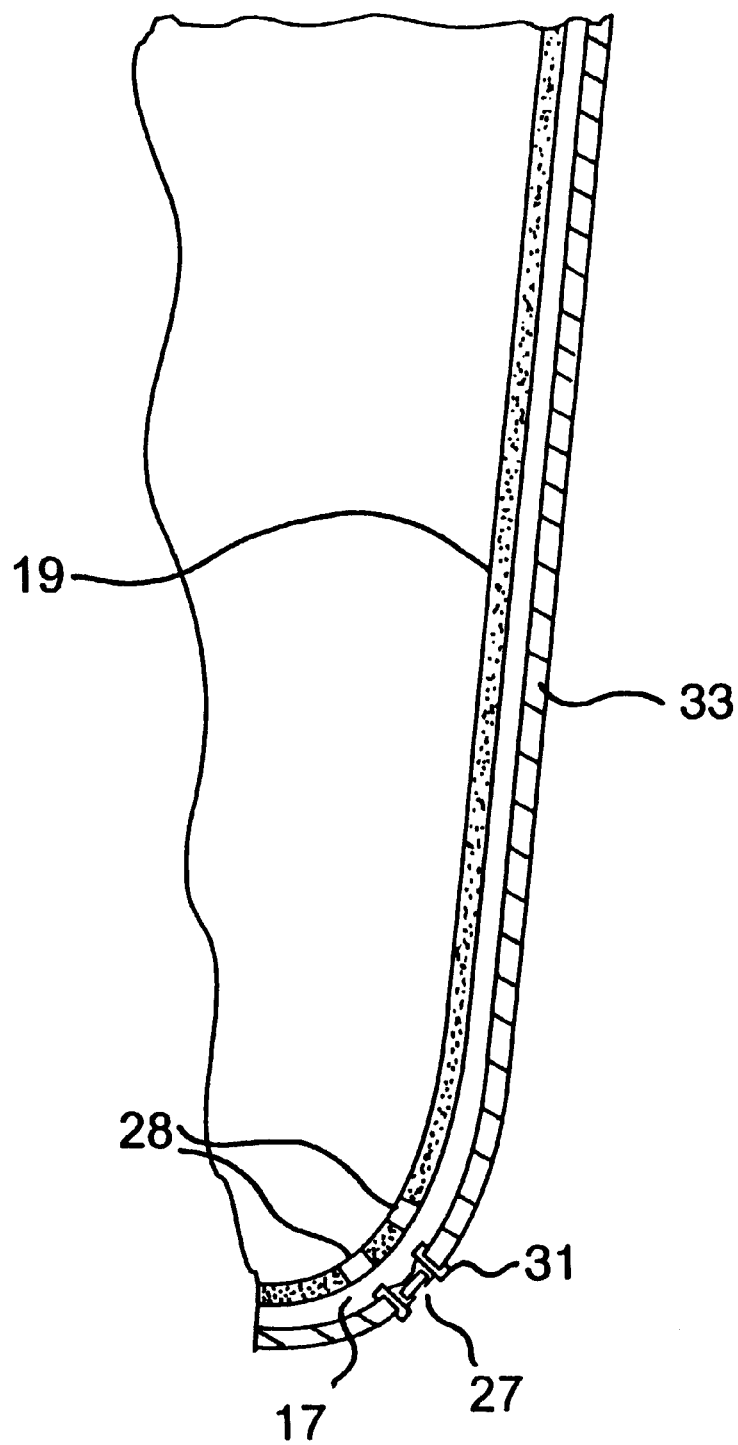
FIG. 3 is a part sectional elevation of the socket and liner of a prosthesis incorporating the third embodiment of the invention.

According to a third embodiment as shown at FIG. 3 if the volume of the interior of the prosthesis between the outer surface of the prosthesis and the socket which provides the space to receive the stump is hollow, the valve and passageway may be incorporated into a plug element 31 which is mounted in to the wall 33 of the socket at the innermost end of the socket. Such a plug 31 can also be used in cases where the socket accommodating the stump is formed by a socket element which also provides the external surface of the prosthesis.

It should be appreciated that the scope of the present invention need not be limited to the particular scope of the embodiments described above. In particular it should be appreciated that in while the first embodiment shown in the accompanying drawing illustrates relates to a prosthesis supporting the stump of the lower leg, the invention is equally applicable to the stump of an upper leg and to prostheses used to replace some or all of the upper limbs.

What is claimed is:

1. An improvement to a prosthesis where said prosthesis comprises a socket which is configured to snugly receive a stump, said improvement comprising a fluid pathway communicating between an exterior of the socket and an outlet at an inner end of the socket, said improvement further comprising a one-way valve located in the fluid pathway and positioned to provide a uni-directional flow of air into the inner end of the socket such that in use the air contacts the stump.

2. An improvement as claimed at claim 1 the outlet comprises a plurality of openings.

3. An improvement as claimed in claim 1 wherein the prosthesis is configured to fit on a leg stump.

4. An improvement as claimed in claim 2 wherein the prosthesis is configured to fit on a leg stump.

5. An improvement as claimed at claim 1, wherein the prosthesis includes a liner which is receivable over the stump and which is receivable in the socket, where the liner is formed with one or more openings in the region of the outlet.

6. An improvement as claimed at claim 2, wherein the prosthesis includes a liner which is receivable over the stump and which is receivable in the socket, where the liner is formed with one or more openings in the region of the outlet.

7. An improvement as claimed at claim 3, wherein the leg prosthesis includes a liner which is receivable over the stump and which is receivable in the socket, where the liner is formed with one or more openings in the region of the outlet.

8. An improvement as claimed at claim 4, wherein the leg prosthesis includes a liner which is receivable over the stump and which is receivable in the socket, where the liner is formed with one or more openings in the region of the outlet.

9. An improvement as claimed at claim 5 wherein the fluid pathway is provided within the body of the liner.

10. An improvement as claimed at claim 6 wherein the fluid pathway is provided within the body of the liner.

11. An improvement as claimed at claim 7 wherein the fluid pathway is provided within the body of the liner.

12. An improvement as claimed at claim 8 wherein the fluid pathway is provided within the body of the liner.

13. An improvement as claimed at claim 1, wherein the fluid pathway is provided by a plug element which is mounted in an aperture in the wall of the socket.

14. An improvement as claimed at claim 2, wherein the fluid pathway is provided by a plug element which is mounted in an aperture in the wall of the socket.

15. An improvement as claimed at claim 3, wherein the fluid pathway is provided by a plug element which is mounted in an aperture in the wall of the socket.

16. An improvement as claimed at claim 4, wherein the fluid pathway is provided by a plug element which is mounted in an aperture in the wall of the socket.

17. A leg prosthesis for accommodating a leg stump of a user, the leg prosthesis comprising:

a socket configured to receive the leg stump therein;

a fluid pathway communicating between an exterior of the socket and an outlet adjacent an inner end of the socket; and a one-way valve located in the fluid pathway for controlling fluid flow through the fluid pathway, said one-way valve designed to permit air flow through the fluid pathway into the inner end of the socket from the exterior of the socket during an upstep of the user such that the air contacts the stump, and said one-way valve is designed to prevent air flow through the fluid pathway from the outlet at the inner end of the socket to the exterior of the socket during a down-step of the user wherein a pressurized cushion of air is created between the stump and the inner end of the socket during the down-step.

* * * * *